United States Patent [19]
More et al.

[11] Patent Number: 5,531,094
[45] Date of Patent: Jul. 2, 1996

[54] APPARATUS FOR TESTING PROSTHETIC HEART VALVE HINGE MECHANISM

[75] Inventors: Robert B. More; Peter Strzepa, both of Austin; Michael J. Mewhort, Pflugerville; Thomas S. Reventas, Austin, all of Tex.

[73] Assignee: Carbomedics, Inc., Austin, Tex.

[21] Appl. No.: 339,476

[22] Filed: Nov. 14, 1994

[51] Int. Cl.$^6$ .................................................. G01M 19/00
[52] U.S. Cl. .................................................. 73/4 R; 73/168
[58] Field of Search .............................. 73/4 R, 168, 37, 73/46, 49.4, 49.8, 865.6

[56] References Cited

U.S. PATENT DOCUMENTS

| | | | |
|---|---|---|---|
| 4,381,663 | 5/1983 | Swanson | 73/37 |
| 4,546,642 | 10/1985 | Swanson | 73/37 |
| 4,682,491 | 7/1987 | Pickard | 73/37 |
| 5,272,909 | 12/1993 | Nguyen et al. | 73/168 |
| 5,406,857 | 4/1995 | Eberhardt et al. | 73/37 |

*Primary Examiner*—Robert Raevis
*Attorney, Agent, or Firm*—John R. Merkling

[57] ABSTRACT

An apparatus for proof testing mechanical heart valve prostheses. The apparatus also provides an in vitro test environment simulating in vivo loads, providing a function test. If the heart valve passes the pivot proof test, a function test is performed. The apparatus first directs a pressurized back flow against the tested valve, closing the valve and applying pressure against the leaflet occluders well beyond the maximum functional in vivo load. The heart valve is positioned so that the leaflets assume their "worst-case" position, that is, the heart valve is oriented so that all the necessary play or gap between the leaflet pivots and pivot recesses is subsumed at one location, thus representing the most severe condition that might be experienced with a heart valve in use. The heart valve is loaded by back pressure applied through a working fluid. Pressure transponders detect the pressure on each side of the heart valve, to determine if a valid test has been performed.

22 Claims, 6 Drawing Sheets

FIG. 8

APPARATUS FOR TESTING PROSTHETIC HEART VALVE HINGE MECHANISM

BACKGROUND OF OUR INVENTION

1. Field of Our Invention

Our invention relates to apparatus for testing mechanical heart valves, and in particular mechanical heart valves having a rigid annulus and one or more pivoting leaflets mounted therein.

2. Description of Related Art

Various types of heart valve prostheses have been proposed, and many give generally satisfactory operation. One popular design for a heart valve prosthesis includes an annular valve body in which a pair of opposed leaflet occluders are pivotly mounted. The occluders are moveable between a closed, mated position, blocking blood flow in an upstream direction, thereby minimizing regurgitation, and an open position, allowing blood flow in a downstream direction. One such heart valve is described, for example, in U.S. Pat. No. 5,147,390 to Campbell, which patent is assigned to CarboMedics, Inc., the assignee of our invention.

A mechanical heart valve, such as that described in the '390 patent, can be expected to open and close a great number of times during its use. It is desirable to minimize, in so far as possible, the number of failures experienced in the use of a prosthetic heart valve. Testing for function is therefore an important part of prosthetic heart valve development and manufacture. Heart valve function testers are known which open and close the mechanical heart valve in an in vitro environment, mimicking the action of the heart. Fluid is forced past the valve to open the valve. An existing back pressure is then allowed to close the valve when the pulsatile forward pressure is removed.

There is, however, another possibility for defects which can be tested. Minute cracks or other surface defects in pivots of leaflet occluders or in pivot recesses of the valve body are difficult to detect. It is known, however, from the application of fracture mechanics, that cracks below a certain maximum size will not cause failure. Cracks or other surface defects larger than the maximum allowable size can be detected by applying a proof test load to the component. The proof test load should be some multiple of the functional in vivo load, to provide a factor of safety associated with the test. The primary purpose of proof testing is to detect components of heart valves with flaws larger than a specific size.

SUMMARY OF OUR INVENTION

We have invented an apparatus for proof testing mechanical heart valve prostheses. The apparatus also provides an in vitro test environment simulating in vivo loads, providing a function test. If the heart valve passes the pivot proof test, a function test is performed. The apparatus therefore first directs a pressurized back flow against the tested valve, closing the valve and applying pressure against the leaflet occluders well beyond the maximum functional in vivo load. The heart valve is positioned so that the leaflets assume their "worst-case" position, that is, the heart valve is oriented so that all the necessary play or gap between the leaflet pivots and pivot recesses is subsumed at one location, thus representing the most severe condition that might be experienced with a heart valve in use. The heart valve is loaded by back pressure applied through a working fluid. Pressure transponders detect the pressure on each side of the heart valve, to determine if a valid test has been performed. Audio sensors can be employed to detect possible failure of a tested valve. After pivot proof testing a function test is performed.

With the foregoing in mind, it is an object of our invention to provide a heart valve tester which proof tests a mechanical heart valve against defects.

It is a further object of our invention to provide a proof tester for mechanical heart valves which will test the heart valve assembly under worse case conditions.

It is another object of our invention to provide a heart valve proof tester which operates in conjunction with function testing.

These and other objects and features of our invention will be apparent from the following detailed description, taken in connection with the accompanying drawings.

DETAILED DESCRIPTION OF OUR PREFERRED EMBODIMENT

We will now describe our preferred embodiment of our invention, with reference to the accompanying drawings.

Figure 1:
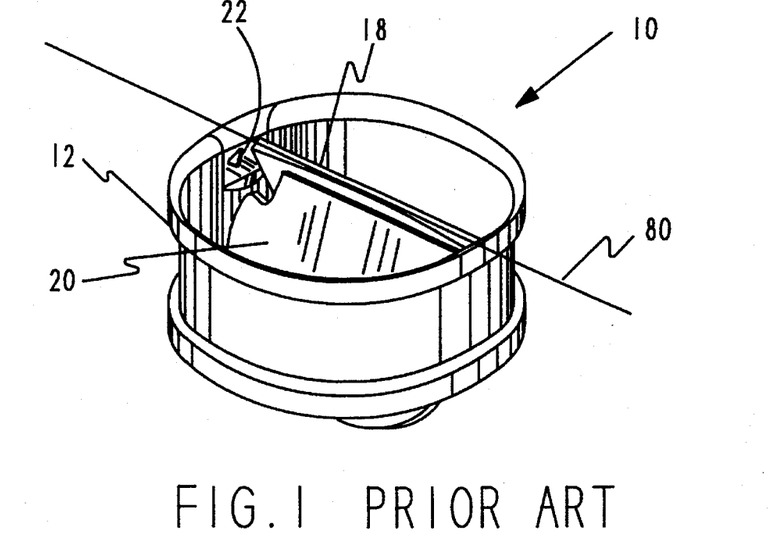
FIG. 1 is a perspective view of an annular valve body and a pair of leaflet occluders from a prosthetic heart valve for testing in the apparatus of our invention.

FIG. 1 illustrates parts of the mechanical heart valve prosthesis generally designated 10, suitable for testing in the apparatus of our invention. Prosthesis 10 includes a generally annular valve body 12. Disposed within the valve body 12 are a pair of leaflet occluders or leaflets, 18, 20. The leaflets 18, 20 are mounted for both pivoting and translational movement between open and closed positions. One leaflet 20 is shown in partial cut-a-way to reveal a pivot recess 22. Two recesses are provided for each leaflet. Each leaflet has a pivot (not shown) which would be received in its adjacent recess. For further explanation of the operation of the heart valve, the reader is referred to U.S. Pat. No. 5,147,390, the disclosure of which is incorporated herein by reference. Further detailed explanation, however, is not necessary for the understanding of our invention. It is well known that mechanical heart valves allow the leaflets 18, 20 to pivot between open and closed positions. A stiffening ring and sewing ring would also usually be added to the annular valve body 12 to complete the prosthesis. Testing, however, preferably occurs prior to adding the stiffening ring and sewing ring.

Figure 2:
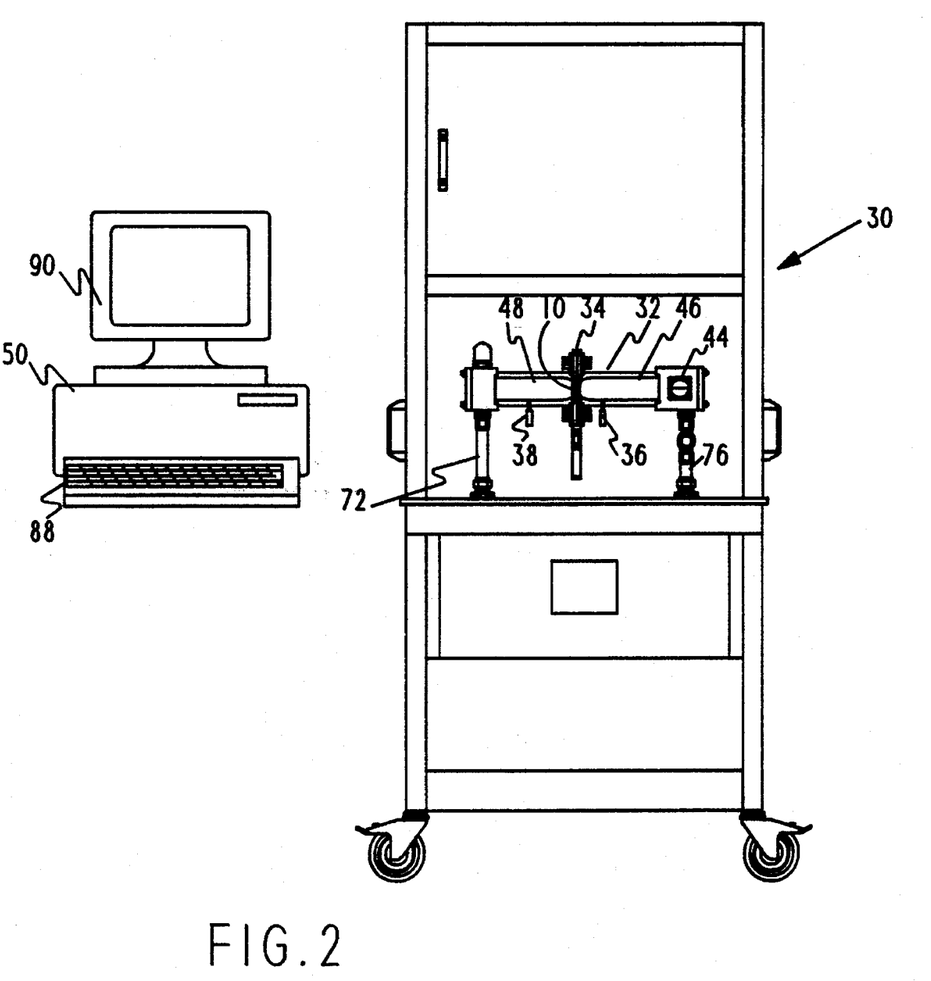
FIG. 2 is a front plan view of a proof tester apparatus for mechanical heart valves in accordance with our invention.
Figure 3:
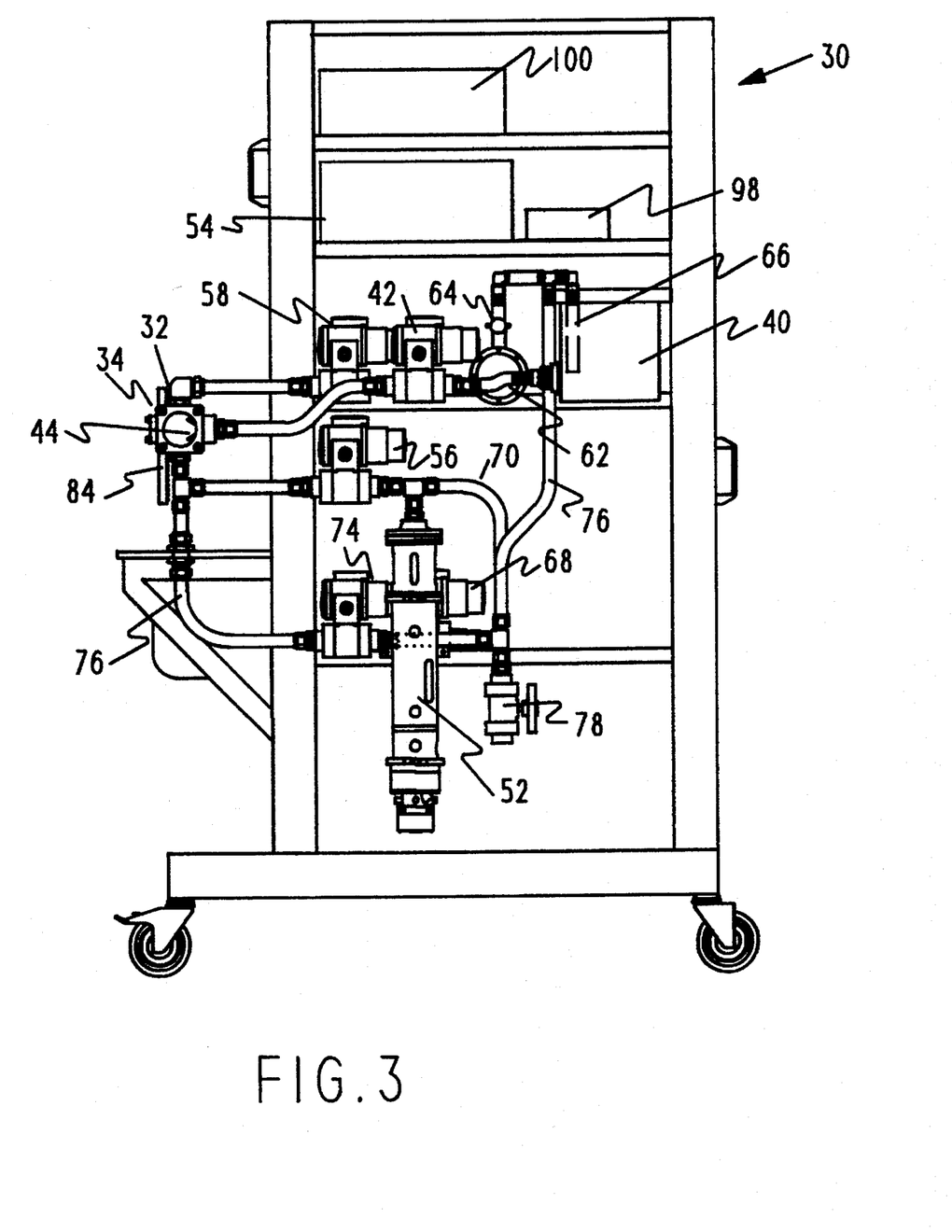
FIG. 3 is a side plan view of the apparatus of FIG. 2.

The test apparatus of our invention is shown in front plan view in FIG. 2 and side plan view in FIG. 3. The apparatus, generally designated 30, comprises a test chamber 32 through which a working fluid, such as purified water, will be forced to test the heart valve assembly 10. A mounting apparatus 34 is provided to hold the heart valve assembly 10 in the desired position within the testing chamber 32. A ventricular pressure transducer 36 and an aortic pressure transducer 38 are provided to sense the pressure on either side of the tested valve.

In the heart valve proof tester apparatus of our invention, the heart valve 10 is tested functionally as if it were implanted in the position of the aortic valve, between the left ventricle of the heart and the aorta. This is the position of greatest pressure within the body and is the position where the valve would experience the highest stresses. The function test, can be understood by reference to FIGS. 2 and 3 and to the diagrammatic function test loop shown in FIG. 5. Working fluid is placed in a catch tank 40. This represents the supply of blood within the body. The working fluid flows by head pressure past a first ball valve 42. The first ball valve 42 and all other ball valves described herein are preferably pneumatically actuated and spring loaded to be normally open when no pressure is applied by action of the control circuits to be described hereafter. Suitable ball valves are available from George Fischer Signet, Inc. of Tustin, Calif. When the first ball valve 42 is open, the working fluid flows out of the catch tank 40 past a mechanical heart valve 44 which acts as a mitral valve and permits the working fluid to flow in only one direction. The working fluid fills a ventricular chamber 46 of the test chamber 32. The heart valve 10, is placed in the mounting apparatus 34 between the ventricular chamber 46 and an aortic chamber 48. The pressure sensors 36, 38 detect the pressures in the ventricular chamber 46 and the aortic chamber 48, respectively, and transmit this information to a controlling microcomputer 50. The microcomputer 50 both gathers data and controls other functions of the test apparatus, as will be more fully described below. A piston pump 52 places the working fluid under periodic pulsatile pressure similar to that which would be produced by the ventricle of a patient's heart. A suitable piston pump is a Superpump System SPS3891 manufactured by Vivitro Systems, Inc., Victoria, B.C., Canada. The piston pump system consists of a piston-in-cylinder pump head driven by a low inertia electric motor. A linear actuator converts rotary motion of the motor to linear displacement of the piston using a lead. The motor is driven by a power amplifier 54. Position and velocity transducers within the pump provide feedback to the power amplifier 54. A complete Pump system includes the amplifier, linear actuator, motor pump head, motor cooling fan and interconnecting cables. The desired oscillatory or pulsatile flows are generated by input of an appropriate wave form from the microcomputer 50 to the power amplifier 54.

Figures 5, 6:
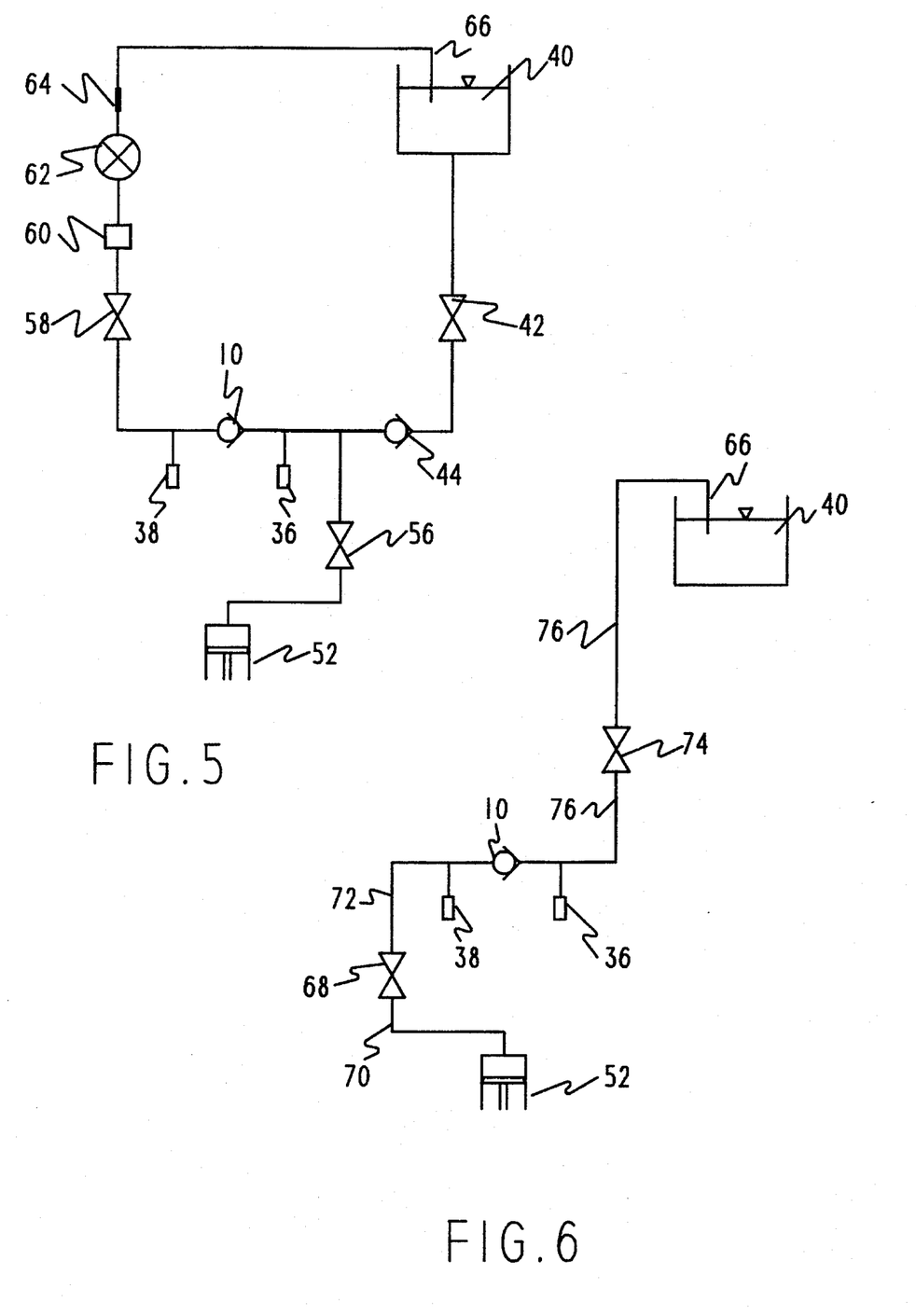
FIG. 5 is a block diagram of a function test flow loop which is part of the complete flow loop of FIG. 4.
FIG. 6 is a proof test flow loop which is part of the complete flow loop of FIG. 4.

Pressurized working fluid driven by the piston pump 52 passes a second ball valve 56 and enters the ventricular chamber 46 between the mitral valve 44 and the test valve 10. During function testing, the action of the piston pump 52 will close the mitral valve 44 and force the test valve 10 open, causing working fluid to flow past the test valve 10. The working fluid will then flow out of the aortic chamber 48 and past a third ball valve 58. A flow meter 60 measures fluid flow and communicates the measurement to the microcomputer 50. An adjustable compliance 62 and an adjustable resistance 64 are used to achieve the desired systolic and diastolic aortic pressure when running the function test. This models the resistance and compliance of the human circulatory system experienced by the valve 10 When implanted. Existence of the resistance and compliance produces a back pressure against the valve 10 which closes the valve between strokes by the piston pump 52. The adjustable resistance 64 can be provided simply by a clamp or other constriction in the flow lines. The adjustable compliance 62 comprises a chamber and diaphragm. A suitable design is described by David W. Wieting in a dissertation "Dynamic Flow Characteristics of Heart Valves", University of Texas at Austin, 1969. Past the adjustable resistance 64, the working fluid is returned to the catch tank 40 through a stand pipe 66.

During the operation of the function test portion of our apparatus, all of the first, second and third ball valves 42, 56, 58 are open, while other ball valves, to be described hereafter, are closed. The flow loop during function testing is represented by the diagram of FIG. 5. The heart valve 10 is subjected to a selected number of cardiac cycles, sufficient to provide the desired function test.

However, before function testing, the heart valve 10 is preferably subjected to a proof test of our invention. The proof test is illustrated diagrammatically in FIG. 6. Under the control of the microcomputer 50, the first, second and third valves 42, 56 and 58 are initially closed, isolating the system described heretofore. A fourth ball valve 68 is opened. The working fluid is driven by the piston pump 52 away from the second ball valve 56 through a back flow tube 70, past the fourth ball valve 68, through a further tube 72 and into the aortic chamber 48 of the test chamber 32. This drives the working fluid under pressure against the heart valve 10, closing the valve. Simultaneously, a fifth ball valve 74 is opened. The fifth ball valve 74 is a line 76 connected to the ventricular chamber 46 of the test chamber 32. Line 76 returns to the stand pipe 66, emptying into the catch tank 40. Opening the fifth ball valve 74 minimizes the pressure in the ventricular test chamber 46. No compliance or resistance is provided in this line so there is little or no back pressure. For convenience, a drain valve 78 may be provided in the line 76 so that the working fluid can be removed from the system. In operation of the proof test, the fourth and fifth valves 68, 74 are opened while the first, second and third valves 42, 56, 58 are closed. A back pressure is applied against the closed valve 10 which exceeds the calculated pressure necessary to provide an energy of fracture against the particular pivot designs selected for test. Under these conditions, it can be expected that defective valves would fail. Use of the working fluid to perform the test prevents development of any new defect.

Figure 4:
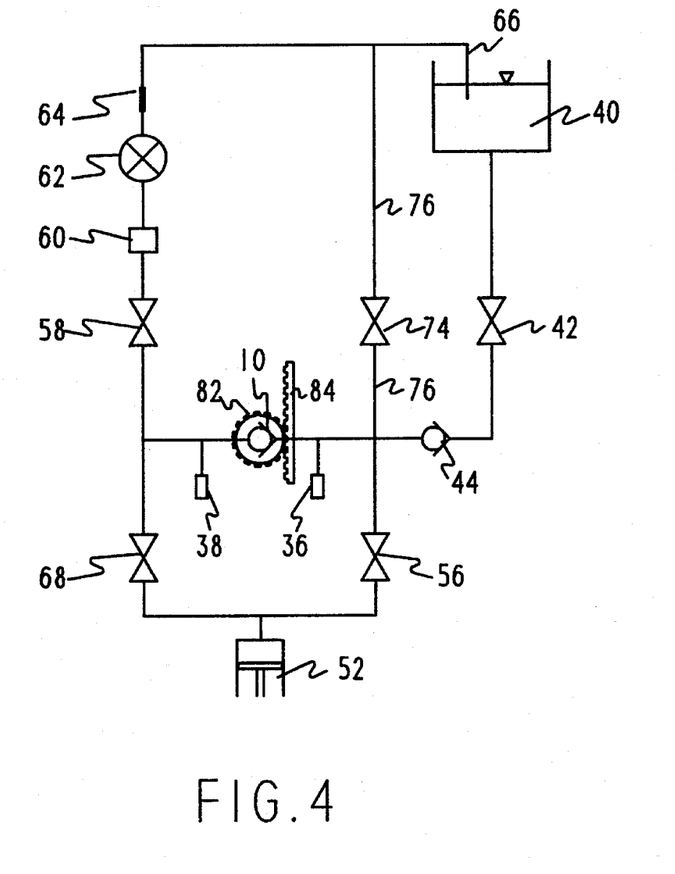
FIG. 4 is a block diagram of a complete flow loop for the apparatus of FIG. 2.

The total fluid system, comprising both the proof test flow loop and the function test flow loop is shown diagrammatically as a complete system in FIG. 4.

In order to test the valve 10 under the most severe conditions, we have also provided a valve holder 34 which reverses the position of the valve 10. Referring to FIG. 1, it is apparent that when the valve 10 is oriented such that a diameter 80 through the pivot recesses is oriented up and down (vertically), the leaflet occluders 18, 20 will tend to fall against one side of the annular body 12. In this condition, the upper pivots will have all of the available play or gap with respect to their associated recesses. This represents the worst case condition for the interaction between the pivots and the recesses. Consequently, it is desirable to test the heart valve in a position where the pivots are oriented upwardly and to reverse the heart valve by 180° so that the, second set of pivots and recesses can also be tested in the worse case condition. To do this, the heart valve holder 34 is provided with a circular pinion gear 82 surrounding the heart valve as illustrated diagrammatically in FIG. 4. A pneumatically driven rack 84 controls the position of the heart valve. After a first proof test is performed with the heart valve in one direction, the microcomputer 50 opens a solenoid 86 to activate the pneumatically driven rack 84, reversing the heart valve. A second proof test would then be performed. Clearly, if a three-leaflet or multiple-leaflet valve were being tested, additional orientations would be selected to accommodate a configuration of the particular valve.

Figure 7:
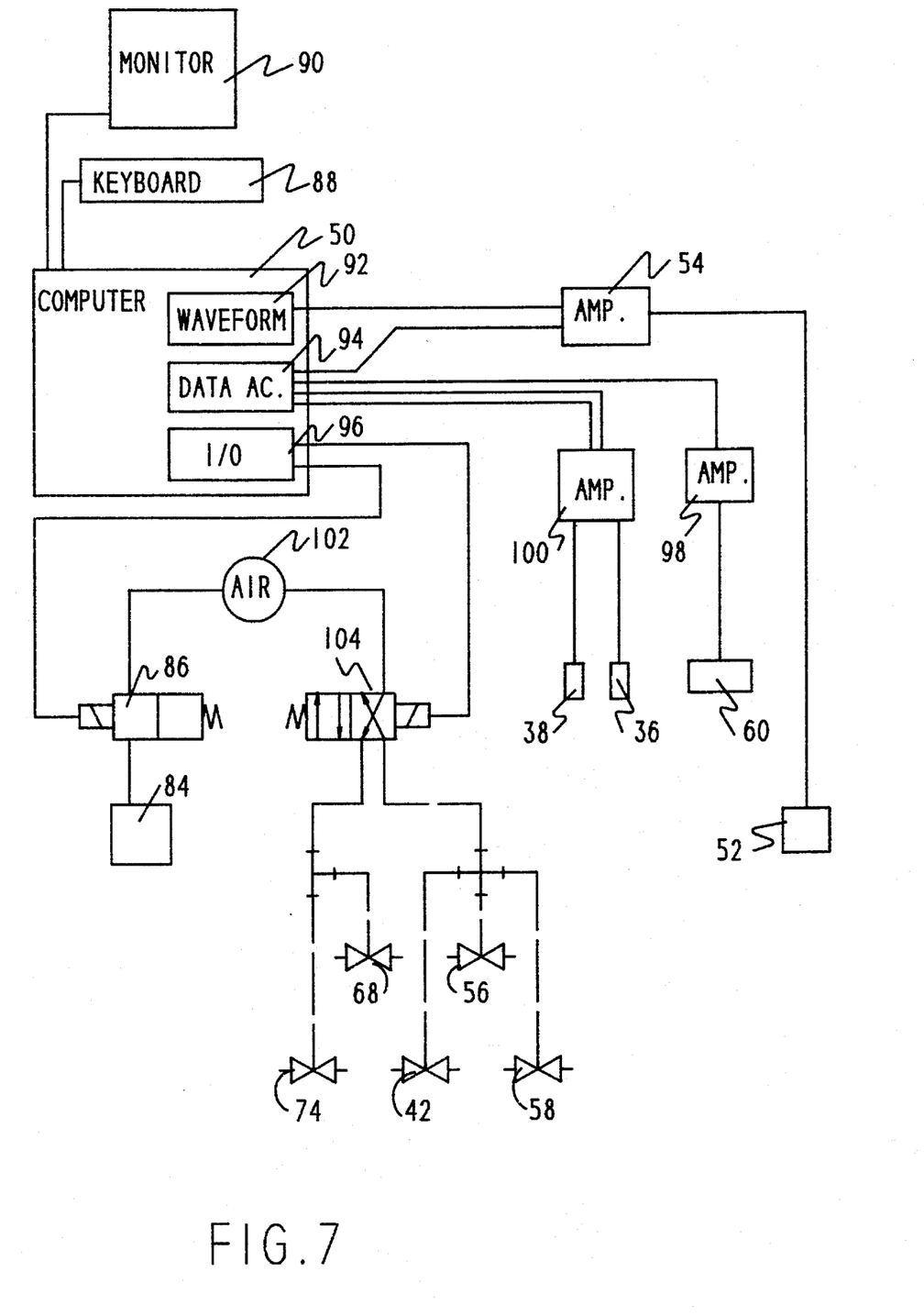
FIG. 7 is a functional block diagram of an electrical and pneumatic control circuit for control of the flow circuit of FIG. 4.

Electrical and pneumatic control of the apparatus 30 can be understood by reference to the diagram of FIG. 7. As shown in FIG. 7, basic control and data acquisition is controlled by a conventional microcomputer 50 having a keyboard 88 and a monitor 90 or other data communication device such as a printer. The computer 50 should also be provided with other specialized interface cards such as a wave-form generator 92, a data acquisition interface 94, and a digital input/output interface 96. The power amplifier 54 controlling the piston pump 52 is controlled by the microcomputer 50 through the wave form generator 92 and gives feedback to the microcomputer 50 through the data acquisition interface 94. The data acquisition interface 94 also receives signals from a flow meter amplifier 98 connected to the flow meter 60 and from a transducer amplifier 100 connected to the ventricular pressure transducer 36 and to the aortic pressure transducer 38. Through the digital input/output interface 96, the microcomputer 50 controls the solenoid valve 86 which operates the pneumatically driven rack 84 of the valve holder 34. The solenoid is supplied with pressured air from an air source 102 such as are commonly available in laboratories.

The microcomputer also controls a second solenoid 104 which is also supplied from the air source 102. The second solenoid 104 supplies air at different times to the ball valves. First, second and third ball valves 42, 56, 58, form a first set of valves which is driven at one time by the solenoid 104. Fourth and fifth ball valves 68, 74 form a second set of valves which are driven oppositely to the first set by the solenoid 104. In other words, when the first set of ball valves is open, the second set is closed and when the second set is open, the first set is closed.

Figure 8:
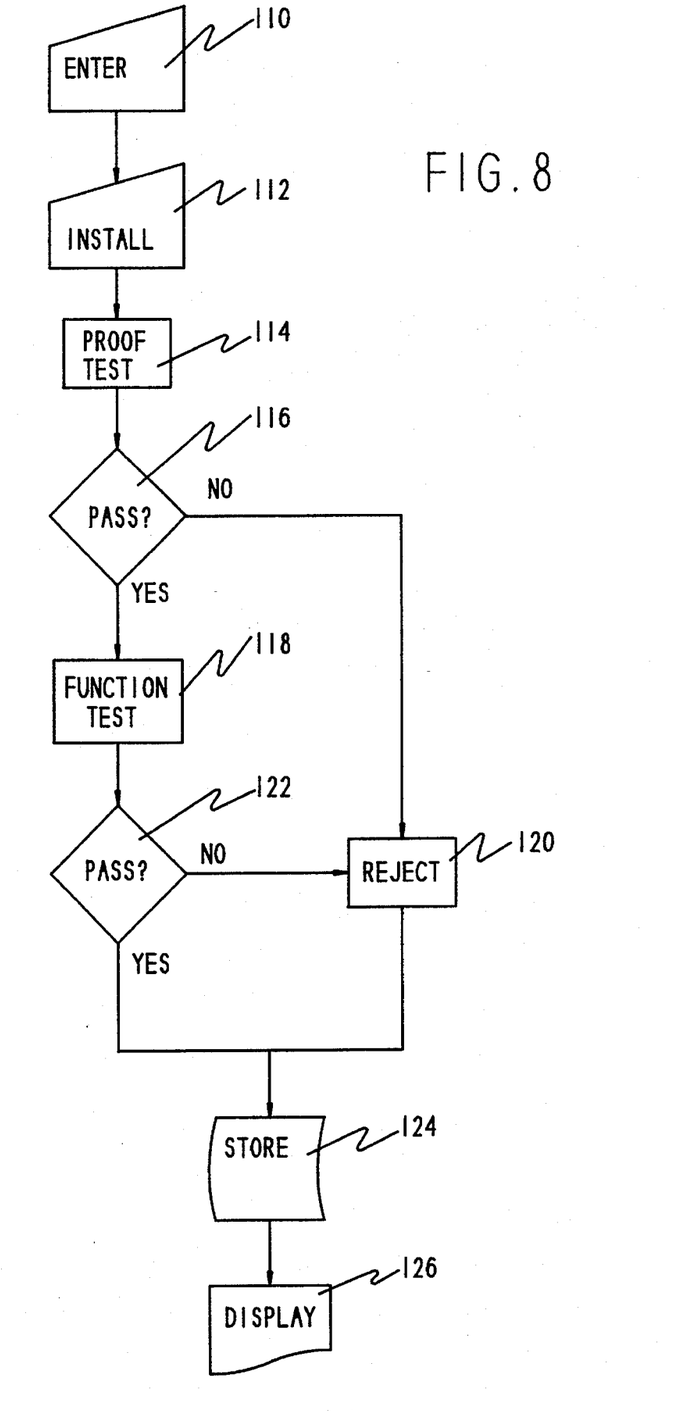
FIG. 8 is a flow chart of a program for controlling the apparatus of FIG. 2.

The function of the microcomputer 50 is also described in FIG. 8 which illustrates a software flow chart. An operator will enter test parameters 110 through the keyboard 88. The operation then pauses at 112 for the operator to install a heart valve for testing. The microcomputer 50 will then execute the proof test at 114 by closing the first set of valves and opening the second set, actuating the proof test loop illustrated in FIG. 6. The microcomputer 50 will control the piston pump 52 to force working fluid against the valve 10. Preferably this pressure will be in excess of 22 psi and preferably between 22 and 23 psi, although a higher pressure can be experienced. It is desirable to closely approximate the desired test pressure, without substantially higher pressures being generated. Our apparatus makes use of the fact that all heart valves allow a certain amount of regurgitation through the valve. The microcomputer 50 therefore controls the piston pump 52 to provide an initial flow rate. The heart valve 10 closes and the pressure in the aortic chamber gradually increases. By detecting the pressure through the pressure sensor 38, it is determined whether the desired pressure in the aortic chamber 48 has been achieved. If not, the flow rate is adjusted, probably upwardly, and pressure is reapplied to the valve. Usually, about three cycles are necessary before the desired level of pressure is obtained. The pressure will then be maintained against the valve for a preselected period of time preferably at least one second.

If it is determined by output of the aortic pressure sensor 38 and the ventricular pressure sensor 36 that the proof test has been passed 116, the microcomputer 50 will proceed to execute the function test at 118. Otherwise the valve will be rejected 120. In the function test 118 the first set of valves will be opened and the second set closed and the piston pump will be controlled to provide a pulsatile flow through the valve 10. The piston pump is actuated through a plurality of cycles until the average aortic pressure, sensed through the aortic pressure transducer 38 stabilizes at a preselected pressure, preferably between 97 and 103 mm Hg, and most preferably 100 mm Hg. When this steady state is reached, the microcomputer 50 begins to acquire data for a predetermined length of time, preferably on the order of 13 seconds. The data acquired is the ventricular and aortic pressures, measured by the ventricular pressure sensor 36 and the aortic pressure sensor 38, and the flow rate, measured by the flow meter 60. Pressure drop and leakage calculations are made from acquired pressure and flow-rate signals. Calculations are made for each of ten consecutive cycles and then averaged to make a final pressure drop and leakage measurement. The valve is rejected 120 if the final pressure drop or final leakage are greater than the predefined acceptance criteria. The acceptance criteria are different for each type and size of valve. The acceptance criteria are set so as to reject any valves that would provide unacceptable performance in vivo. If the function test 122 is passed, the result of the data is saved to internal memory 124 by the microcomputer 50. The data may also be displayed 126 either on the monitor 90 or off an output device such as a printer.

A description of the present form of our invention having been made by way of example, it is anticipated that further variations of the apparatus may be made without departing from the invention and the scope of the appended claims.

We claim as our invention:

1. An apparatus for proof testing at least part of a mechanical prosthetic heart valve, said part including at least one leaflet and a valve body holding said leaflet, said apparatus comprising means for holding said part of said mechanical prosthetic heart valve in a selected position for proof testing, means for directing a working fluid against said at least one leaflet and for forcing said leaflet into a closed position impeding flow of said working fluid, and means for maintaining an elevated back pressure against said leaflet for a selected period of time, said back pressure exceeding 22 psi and being sufficient to provide a selected energy of fracture.

2. An apparatus for proof testing at least part of a mechanical prosthetic heart valve, said part including at least one leaflet and a valve body holding said leaflet, said apparatus comprising means for holding said part of said mechanical prosthetic heart valve in a selected position for proof testing, means for turning said part to selected worse-case orientations, means for directing a working fluid against said at least one leaflet and for forcing said leaflet into a closed position impeding flow of said working fluid, and means for maintaining an elevated back pressure against said leaflet for a selected period of time, said back pressure being sufficient to provide a selected energy of fracture.

3. The apparatus according to claim 2 wherein said means for turning comprise a rack and a pinion gear.

4. The apparatus according to claim 2 further comprising means for sensing said elevated back pressure.

5. The apparatus according to claim 4 further comprising means for incrementally raising said back pressure to a preselected test pressure.

6. The apparatus according to claim 5 wherein said means for directing a working fluid comprise means for controlling a rate of flow of said working fluid, and wherein said means for incrementally raising said back pressure comprise means for incrementally raising said rate of flow.

7. The apparatus according to claim 6 wherein said means for incrementally raising said rate of flow is responsive to said means for sensing to adjust said rate of flow.

8. The apparatus according to claim 2 further comprising means for selectively applying a pulsatile forward flow of said working fluid through said part of said mechanical heart valve at a systolic pressure of physiologic magnitude.

9. The apparatus according to claim 8 further comprising a fluid flow compliance and a fluid flow resistance for creating a diastolic pressure between pulses of said pulsatile forward flow.

10. The apparatus according to claim 2 wherein said back pressure exceeds 22 psi.

11. A method for proof testing at least part of a mechanical prosthetic heart valve, said part including at least one leaflet and a valve body holding said leaflet, said method comprising the steps of holding said part of said mechanical prosthetic heart valve in a selected position for proof testing, directing a working fluid against said at least one leaflet and for forcing said leaflet into a closed position impeding flow of said working fluid, and maintaining an elevated back pressure against said leaflet for a selected period of time, said back pressure exceeding 22 psi and being sufficient to provide a selected energy of fracture.

12. A method for proof testing at least part of a mechanical prosthetic heart valve, said part including at least one leaflet and a valve body holding said leaflet, said method comprising the steps of holding said part of said mechanical prosthetic heart valve in a selected position for proof testing, turning said part to selected worse-case orientations, directing a working fluid against said at least one leaflet and for forcing said leaflet into a closed position impeding flow of said working fluid, and maintaining an elevated back pressure against said leaflet for a selected period of time, said back pressure being in excess of expected diastolic pressure.

13. The method according to claim 12 wherein said step of turning comprise inverting said part of said heart valve.

14. The method according to claim 13 further comprising sensing said elevated back pressure.

15. The method according to claim 14 further comprising incrementally raising said back pressure to a preselected test pressure.

16. The method according to claim 15 wherein said step of directing a working fluid comprises controlling a rate of flow of said working fluid, and wherein said step of incrementally raising said beck pressure comprise incrementally raising said rate of flow.

17. The method according to claim 16 wherein said step of incrementally raising said rate of flow is responsive to said means for sensing to adjust said rate of flow.

18. The method according to claim 12 further comprising the step of selectively applying a pulsatile forward flow of said working fluid through said part of said mechanical heart valve at a systolic pressure of physiologic magnitude.

19. The method according to claim 18 further comprising the step of creating a fluid flow compliance and a fluid flow resistance to impose a diastolic pressure between pulses of said pulsatile forward flow.

20. The method according to claim 12 wherein said back pressure exceeds 22 psi.

21. An apparatus for proof testing at least part of a mechanical prosthetic heart valve, said part including at least one leaflet and a valve body holding said leaflet, said apparatus comprising means for holding said part of said mechanical prosthetic heart valve in a selected position for proof testing, means for directing a working fluid against said at least one leaflet and for forcing said leaflet into a closed position impeding flow of said working fluid, said means for directing a working fluid comprising means for controlling a rate of flow of said working fluid, means for maintaining an elevated back pressure against said leaflet for a selected period of time, said back pressure being sufficient to provide a selected energy of fracture, means for sensing said back pressure, means for incrementally raising said flow rate to attain said elevated back pressure.

22. The apparatus according to claim 21 wherein said means for incrementally raising said rate of flow is responsive to said means for sensing to adjust said rate of flow.

* * * * *